United States Patent [19]
Lowe et al.

[11] Patent Number: 5,775,328
[45] Date of Patent: Jul. 7, 1998

[54] DEVICE FOR USE IN TEMPORARY INSERTION OF A SENSOR WITHIN A PATIENT'S BODY

[76] Inventors: Robert L. Lowe, 450 SW. 88th Ave.; Anthony P. Furnary, 7266 SW. Eton Ct., both of Portland, Oreg. 97225

[21] Appl. No.: 672,484

[22] Filed: Jun. 26, 1996

[51] Int. Cl.⁶ .................................................. A61B 8/00
[52] U.S. Cl. ............................................... 128/662.06
[58] Field of Search ....................... 128/662.05, 662.06, 128/637, 772, DIG. 26; 604/27

[56] References Cited

U.S. PATENT DOCUMENTS

| | | | |
|---|---|---|---|
| 3,878,849 | 4/1975 | Muller et al. | 128/DIG. 26 |
| 4,100,309 | 7/1978 | Micklus et al. | 427/2 |
| 4,408,612 | 10/1983 | Utsugi | 128/662.06 |
| 4,671,295 | 6/1987 | Abrams et al. | 128/663 |
| 4,722,347 | 2/1988 | Abrams et al. | 128/663 |
| 4,886,059 | 12/1989 | Weber | 128/207.15 |
| 4,947,854 | 8/1990 | Rabinovitz et al. | 128/662.04 |
| 5,205,292 | 4/1993 | Czar et al. | 128/662.03 |
| 5,265,612 | 11/1993 | Sarvazyan et al. | 128/662.06 |
| 5,284,146 | 2/1994 | Czar et al. | 128/662.03 |
| 5,291,896 | 3/1994 | Fonger et al. | 128/713 |
| 5,331,947 | 7/1994 | Shturman | 128/662.06 |
| 5,335,663 | 8/1994 | Oakley et al. | 128/662.06 |
| 5,443,445 | 8/1995 | Peters et al. | 604/27 |

*Primary Examiner*—George Manuel
*Attorney, Agent, or Firm*—Chernoff, Vilhauer, McClung & Stenzel

[57] ABSTRACT

A device for use in placing a non-sterile sensor probe such as an ultrasound scanning transducer in a desired position within a patient's body, with a probe-receiving tube having a closed distal end so that a probe inserted within the tube through an open proximal end located outside the patient's body is isolated from contact with or contamination of the interior of the patient's body. The probe-receiving tube is attached to and extends alongside an elongate support member which aids in placement of the probe-receiving tube in a location proximate an organ to be observed by use of a sensor probe in the probe-receiving tube. The elongate support tube may be a chest drain tube.

20 Claims, 2 Drawing Sheets

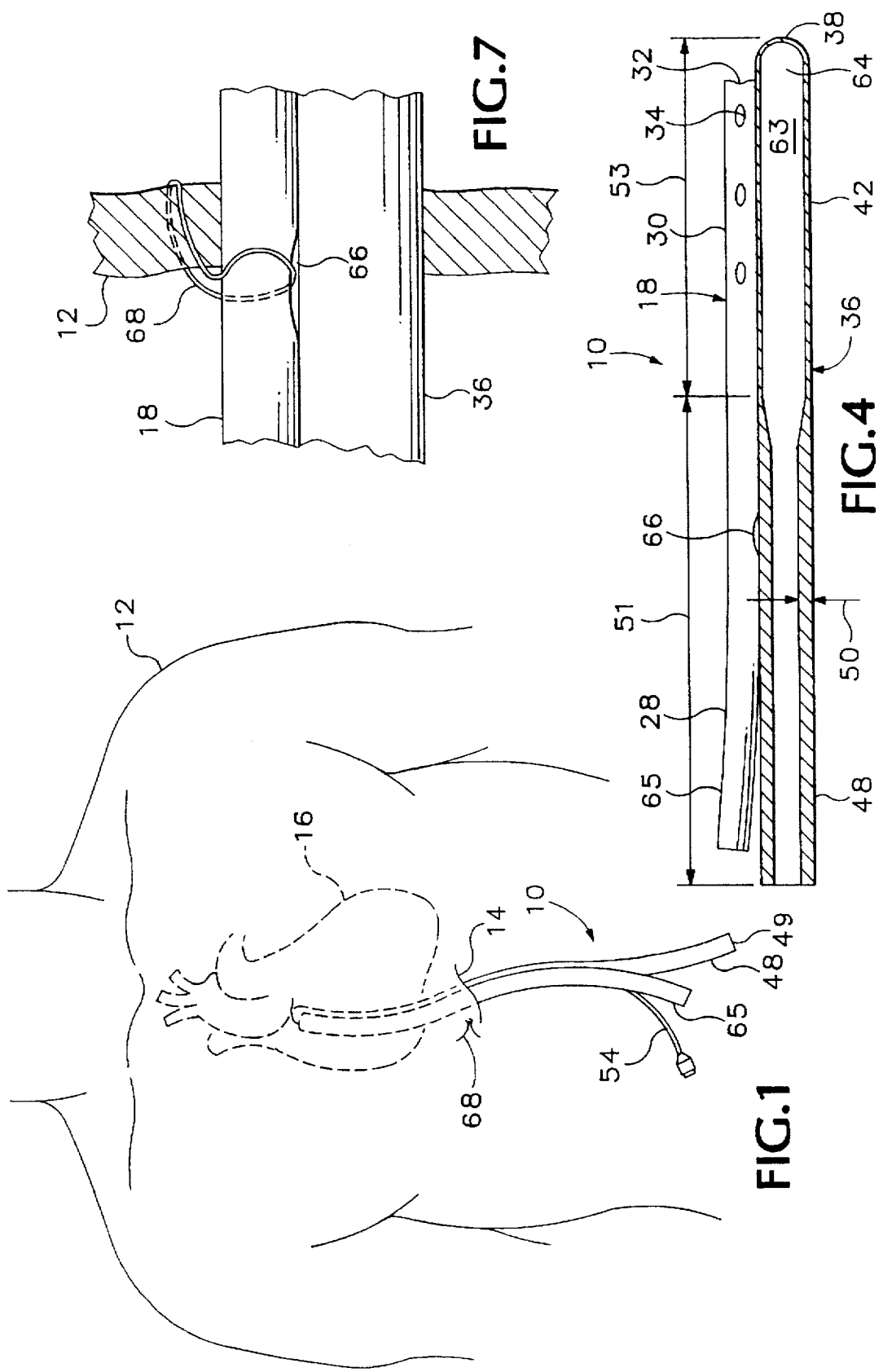

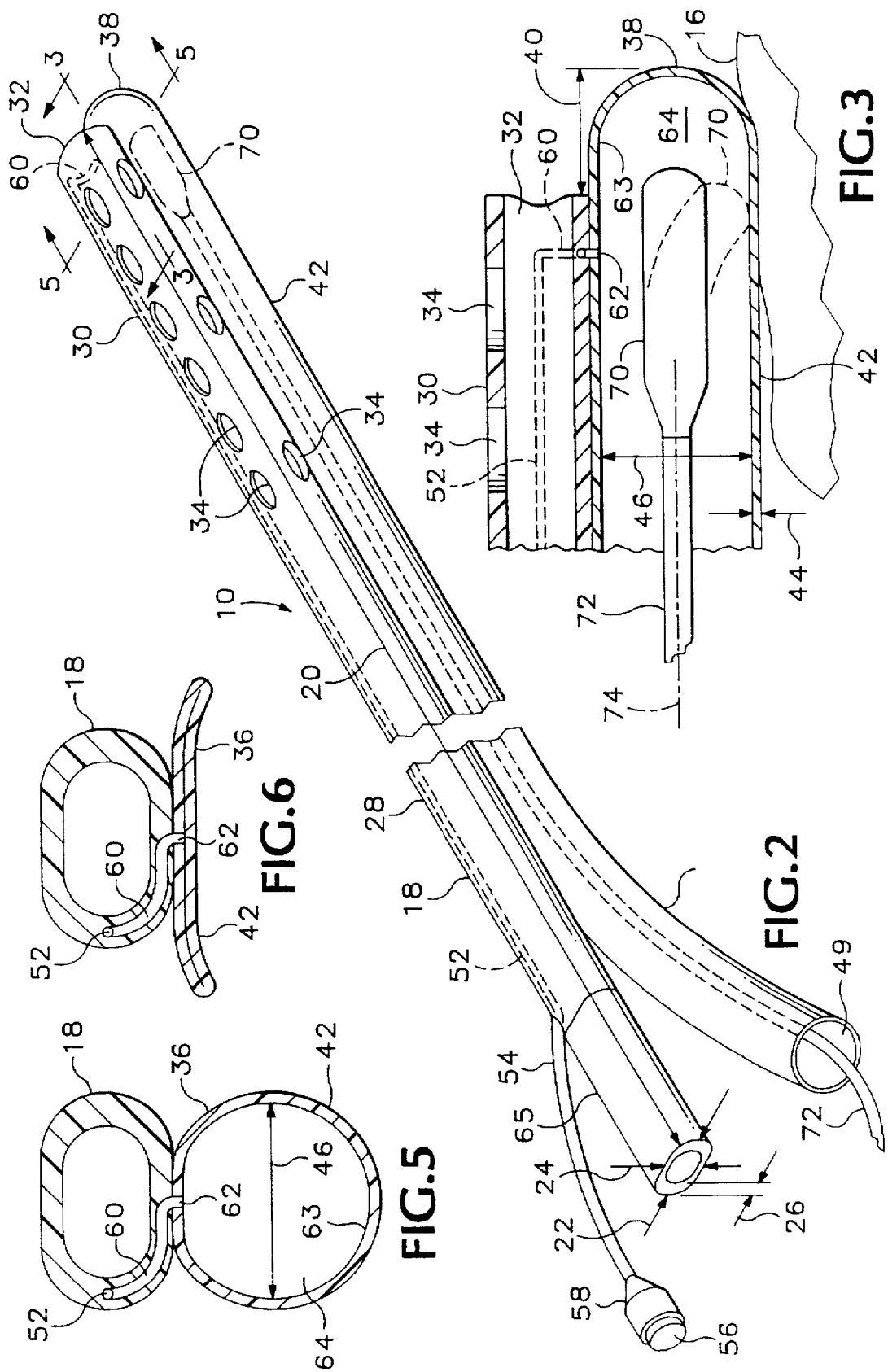

1

DEVICE FOR USE IN TEMPORARY INSERTION OF A SENSOR WITHIN A PATIENT'S BODY

BACKGROUND OF THE INVENTION

The present invention relates to placement of sensors within a patient's body, and in particular relates to facilitating repeated placement of a non-sterile ultrasound transducer into a patient's body in a minimally invasive and sterile manner.

It is frequently desirable to obtain information regarding the size, shape, and function of internal body organs by the use of ultrasound echo imaging. For example, it is desirable to evaluate the performance of a patient's heart after cardiac surgery. In the time immediately after such surgery, patients frequently have significant cardiac functional problems, and visualization and examination of the heart by ultrasound echo imaging may be of critical value. Currently, transthoracic and transesophageal echocardiography are performed as manners of observing the heart. These are not entirely desirable, however, as the second requires sedation and presents risks of trauma to the esophagus and the images obtained by the first are of poor quality after cardiac surgery.

Fonger et al. U.S. Pat. No. 5,291,896 discloses a sterile cardiac probe inserted through an open-ended lumen of a flexible chest drain tube having one end extending into the thoracic cavity of a patient. The probe is surgically fastened to the aorta or the pulmonary artery of the patient in order to obtain information relating only to the volume of flow of blood through such vessels.

Czar et al. U.S. Pat. No. 5,205,292 discloses a removable surgically implanted sterile transducer for attachment to a blood vessel in order to evaluate the volume of blood flow in the vessel.

Abrams et al. U.S. Pat. No. 4,671,295 discloses a method and apparatus for measuring cardiac output through the use of a transducer introduced into the patient's trachea to transmit and receive ultrasound waves and evaluate the flow of blood in the ascending aorta through the use of Doppler frequency differences.

Weber U.S. Pat. No. 4,886,059 discloses an endotracheal tube including a transducer assembly disposed to transmit ultrasound waves in selected directions through the tracheal wall to collect Doppler data for blood flow velocity calculation and to calculate the diameter of the artery.

None of the devices disclosed in the patents discussed above, however, provides for placement of a non-sterile ultrasound transducer in a desired position within a sterile body cavity of a patient quickly, easily and repeatedly, nor does any of them provide a way of obtaining scanned ultrasound two-dimensional echo images of internal organs without having to transmit the ultrasound waves into the body from an external location.

What is desired, then, is a device and a method for its use in permitting, a non-sterile sensor such as an ultrasound scanning transducer to be introduced into a body cavity of a patient quickly and easily in a sterile fashion, and without performing additional surgical procedures or sedation as part of the introduction of the transducer. It is also desired to provide for removal and later temporary reintroduction of a non-sterile sensor without further surgical procedures or sedation.

SUMMARY OF THE INVENTION

The present invention provides an answer to the need explained above by providing a sterile probe-receiving tube which makes available a sterilely protected non-sterile space within a patient's body where a sensor probe may be inserted when necessary, either to be left in place or removed and reinserted later, as necessary. In accordance with the invention such a probe-receiving tube is supported by an elongate support member, which ay have other supportive functions, attached to and extending along at least a distal portion of the probe-receiving tube, and a proximal portion of the probe-receiving tube is available outside the patient's body as an entrance through which to insert a non-sterile probe into the interior of the patient's body. In one embodiment of the invention a proximal portion of the elongate support member is available outside the patient's body for use if necessary to adjust the location of the probe enclosed within the probe-receiving tube attached to it.

In a device which is one embodiment of the invention the elongate support member is in the form of a chest drain tube placed within the thoracic cavity of a cardiac surgery patient prior to closing the patient's chest, with the proximal portion of the device being located externally of the patient's abdomen and the distal portion of the device extending through an opening in the abdominal wall and thence toward the patient's heart, so that the probe-receiving tube is available in a desired position to provide an ultrasound two-dimensional echo image of the patient's heart or continuous-wave pulse gated, and color flow Doppler ultrasound data during the post-surgery period when it is critical to evaluate the function of the heart.

In a preferred embodiment of the invention a conduit may be provided through which to introduce an acoustic coupling medium into the distal portion of the probe-receiving tube to enable such an ultrasound transducer probe to provide a desired image efficiently. Since the distal end of the probe-receiving tube of a device according to the invention is closed, the internal space within the probe-receiving tube is isolated from the interior of the patient's body cavity, and introduction of a non-sterile sensor probe or of material introduced through the conduit as an acoustic coupling agent cannot result in contamination of the patient's body cavity.

In one embodiment of the invention a passage is provided to receive a fastener such as a suture to retain the elongate support member in a desired position with respect to the patient's body without constricting the probe-receiving tube.

In accordance with the method of the invention a sensor probe can be placed quickly and easily in a desired location within a patient's body by inserting it into the patient's body through the probe-receiving tube at any time after the probe-receiving tube, supported by the elongate supporting member, has been installed.

Thus, according to the method of the invention, a non-sterile ultrasound probe may be inserted through the probe-receiving tube into a position proximate an internal organ such as a patient's heart to obtain an ultrasound echo image of the organ as by providing an ultrasound image of the heart at a time subsequent to the completion of cardiac surgery.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 1 is a simplified view of a patient's torso, showing a device embodying the present invention in place.

FIG. 2 is a perspective view of a combined chest drain tube and probe-receiving tube according to the present invention.

FIG. 3 is a sectional view of part of a distal end portion of the combined chest drain tube and probe-receiving tube shown in FIG. 2.

FIG. 4 is a side elevational view of the combined chest drain tube and probe-receiving tube shown in FIGS. 1–3, with the probe-receiving tube shown in sectional view.

FIG. 5 is a sectional view, taken along line 5—5 of FIG. 2.

FIG. 6 is a sectional view taken along line 5—5 of FIG. 2, with the distal end portion of the probe-receiving tube in a collapsed condition.

FIG. 7 is a simplified view showing a short portion of the combined drain tube and probe-receiving tube shown in FIG. 1, with the combined tubes extending through the abdominal wall of a patient, and showing a suture holding the drain tube in its required location.

DETAILED DESCRIPTION OF THE PREFERRED EMBODIMENT

Referring now to the drawings which form a part of the disclosure herein, an access-providing device 10 embodying the present invention is shown in place in a cardiac surgery patient 12, with the device extending into the interior of the thoracic cavity of the patient 12 through a surgical opening 14 beneath the sternum, so that a sensor can later be positioned within the device 10 in a desired location within the thoracic cavity of the patient, in order to obtain, for example, an ultrasound image of the patient's heart 16.

As shown in greater detail in FIGS. 2, 3, and 4, the device 10 includes a chest drain tube 18, preferably of a type manufactured by Axiom Medical, Inc., of Rancho Dominguez, Calif. Such a chest drain tube 18 is of a resiliently flexible silicone rubber material which is clear and translucent and suitable for biomedical applications. One satisfactory material for the drain tube 18 has, for example, a Shore A hardness of 60±5 durometer, at least 1100 psi tensile strength, at least 600% elongation, and tear-resistance of at least 130 pounds per inch. These characteristics are not critical, but what is necessary is for the drain tube 18 to be suitable for biomedical use and to be somewhat flexible. The chest drain tube 18 shown herein as an example has a length 20 of about 445 mm and is oval in cross-section, having a width 22 of about 1.8 cm and a height 24 of about 9 mm, but these dimensions are not critical to the present invention. A maximum wall thickness 26, at one end of the oval cross-section shape, may be about 2.5 mm.

A proximal portion 28 of the chest drain tube 18 normally remains outside the body of a patient, while the drain tube 18 extends through the surgical opening 14 and a distal end portion 30 is in position in the pericardial space to remove blood following open heart surgery. The blood can enter into the lumen of the chest drain tube through the open distal end 32 and several openings 34 defined through the wall of the distal end portion 30.

Extending along and attached to the distal end portion 30 and a part of the proximal portion 28 is a probe-receiving tube 36, for which the chest drain tube 18 acts as an elongate support member. The probe-receiving tube 36 is of a biologically compatible and ultrasound translucent material such as a silicone rubber similar to that of the chest drain tube 18, in a preferred embodiment of the invention. The probe-receiving tube 36 has a thin, flexible wall and is generally oval or circular in cross-section, as may be seen best in FIG. 5. It has a closed distal end 38 which may be generally hemispherical, and which extends beyond the open distal end 32 of the drain tube 18 by a distance 40 of at least about 5 mm and preferably about 5 mm. A distal portion 42 and the closed distal end 38 of the probe-receiving tube 36 have a wall thickness 44 of about 0.4 mm and an inside diameter 46 of about 16 mm (36 French). The wall thickness 44 is small enough that it allows the distal portion 42 of the probe-receiving tube 36 to collapse easily or to conform easily to the shape of an object pressing against its outside surface. As may be seen most clearly in FIG. 4, a proximal portion 48 of the probe-receiving tube 36 has a length 51 of about 28 cm and has a greater wall thickness 50, for example 1.2 mm so that it has a greater tendency to retain its circular shape, for reasons which will be made apparent presently.

The distal portion 42 has a length 53 of about 24 cm, for example. The distal portion 42 and a part of the proximal portion 48 of the probe-receiving tube 36 extend along and are securely adhered to the chest drain tube 18, as shown best in FIGS. 4, 5 and 6.

A small tubular conduit 52 is defined within the wall of the chest drain tube 18 and communicates with a branch tube 54 extending away from the proximal portion 28. The branch tube 54 may be closed off tightly, as by a plug 56 fitting in an end coupling 58 which may be formed as an integral part of the branch tube 54. Near the distal end 32 of the drain tube 18, an interconnecting portion 60 of the small conduit 52 extends circumferentially of the drain tube 18 within its wall to an internal port 62, shown in FIGS. 3, 5 and 6, opening into the interior space 64 within the probe-receiving tube 36.

Preferably, the interior surface 63 of the probe-receiving tube 36, defining an interior space 64, is coated with a friction-inhibiting material which makes the interior surface very slippery when it is wetted by water or blood. This material resists adhesion and clotting of blood and is also used on the interior and exterior surfaces of the chest drain tube 18. A coating material suitable for this purpose is a polyvinyl-pyrollidone-polyurethane interpolymer, as disclosed in Micklus et al. U.S. Pat. No. 4,100,309, for example, available from Axiom Medical, Inc. of Rancho Dominguez, Calif. under the trademark Clot-Stop.

The proximal end part 65 of the proximal portion 28 of the chest tube 18, extending proximally from the point of insertion of the branch tube 54, does not include a lumen corresponding to small conduit 52. The proximal end part 65 may be formed as a separate piece of similar tubing without such a small lumen, joined to the portion of the chest drain tube 18 which does include the small conduit 52, so that there is no open end of the small conduit 52 exposed to possible contamination.

As shown in FIGS. 4 and 7, a transversely-extending fastener passageway 66 is defined between the chest drain tube 18 and the probe-receiving tube 36, to permit a suture 68, or a similar fastener, to encircle the chest drain tube 18 to fasten it in place where it extends through the surgical opening 14, as shown in FIG. 7, without constricting the probe-receiving tube 36.

Referring once more to FIG. 1, the access-providing device 10 may be used for a patient whose chest has been opened for cardiac surgery, by inserting the distal end part 30 of the drain tube 18, together with the attached distal portion 42 of the probe-receiving tube, through the surgical opening 14 and into the pericardial space within the patient 12. A suture 68 is used to fasten the device 10 in place with the proximal portion 48 of the probe-receiving tube 36 preferably resting against the right ventricle of the patient's heart 16. The openings 34 are thus left available, unobstructed, to provide the required drainage of the pericardial space once the patient's chest has been closed in completion of surgery. The probe-receiving tube 36 is thus kept properly located and available to receive a probe such as a steerable ultrasound transducer probe 70 which can be inserted into the distal end 43 of the probe-receiving tube 36, supported by an encapsulated cable 72 of conventional form. The size of the interior space 64 defined within the probe-receiving tube 36 is ample to admit an ultrasound probe 70 of the size and type well known for use transesophageally in adults, such as a piezoelectric transducer available from Hewlett-Packard, Advanced Technology Laboratory, or Accuson. A transducer probe 70 of smaller size may be utilized if available. The transducer cable 72 is preferably of a type which is controllably bendable and allows the transducer probe 70 to be reoriented to transmit ultrasound vibrations in various directions as illustrated by the position of the transducer probe 70 shown in broken line in FIG. 3. Additionally, the cable 72 and the ultrasound transducer probe 70 may be rotated about the longitudinal axis 74 of the cable 72, to obtain an ultrasound image in a desired direction. The distal end portion 38 of the probe-receiving tube 36, extending beyond the distal end 32 of the drain tube 18, permits unobstructed transmission and reception of the ultrasound waves by the transducer probe 70 in any direction relative to the axis 74.

Preferably, the usual placement of the chest drain tube 18, extending into the body cavity of the patient 12 through the right rectus muscle and fascia in an orientation slightly divergent from vertical, brings the probe-receiving tube 36 into contact with the anterior surface of the epicardium of the right ventricle of the patient's heart 16. The position of the access-providing device 10 can be adjusted by the surgeon during surgery, before closure of the chest, and the suture 68 can be used to keep the entire device 10 in the proper location, to permit repeated insertion and removal of the transducer 70 through the probe-receiving tube 36 so long as the device 10 is left in place.

To assure good acoustic coupling, particularly where the transducer 70 may not be in intimate contact with the interior surface 63 of the probe-receiving tube 36, a quantity of a liquid acoustic coupling medium, such as water, may be introduced into the branch tube 54 through the end coupling 58 to displace air surrounding the transducer probe 70 within the interior space 64.

The greater wall thickness 50 in the proximal portion 48 of the probe-receiving tube 36 provides additional ability to resist collapsing during insertion of a probe such as an ultrasound transducer. This facilitates pushing the probe 70 and its cable 72 into the proper position within the probe-receiving tube 36, without wrinkling the part of the proximal portion 48 that is unattached to the drain tube 18. The portion of the probe-receiving tube 36 which is securely attached along-side the drain tube 18 is less likely to wrinkle and impede insertion of the probe transducer 70, particularly if the interior surface of the probe-receiving tube 36 is coated with the previously-described friction-reducing coating and has been wetted as by insertion of fluid through the branch tube 54 and the small conduit 52. Since the interior space 64 within the probe-receiving tube 36 is entirely isolated from possible contact with the interior of the body of the patient 12, it need not be sterile, and it is possible to insert the ultrasound transducer probe 70 temporarily into the probe-receiving tube 36 at various times as required or desired for observation of the function of the patient's heart following surgery. Therefore, it is not absolutely necessary to keep the proximal end 49 closed and clean.

When the probe 70 and its cable 72 are not located within the interior space 64, the distal portion 48 of the probe-receiving tube 36 is free to collapse under the pressures encountered within the body cavity where the probe-receiving tube is located, as shown in FIG. 6. At the same time, the greater wall thickness 50 keeps the proximal portion of the probe-receiving tube 36 open to receive a transducer probe 70 and cable 72.

When the drain tube and the probe-receiving tube are no longer needed the suture 68 may be removed releasing the device 10 to be withdrawn, and the opening 14 can be closed.

While the invention has been described above in connection with one preferred embodiment, it will be understood that the probe-receiving tube 36 of the invention may be unsupported or supported by an elongate support member of a different construction and can be utilized for repeated temporary insertion and removal of a medical sensor such as an ultrasound transducer probe in different internal cavities of the body of a patient 12 either briefly or over an extended time of as much as several days. The probe-receiving tube of the invention thus can be used in order to scan organs within the patient's body with ultrasound or provide ultrasound transmissions for purposes of obtaining Doppler measurements, either through an opening such as the surgical opening 14, or through a natural orifice of the patient's body, such as the trachea, urethra and bladder, or rectum, so that ultrasound wave propagation to and from the organ is more direct than when transmitted through the patient's skin and layers of external tissue or bones.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A device for use in a medical procedure for placing a sensor probe temporarily in a desired location within a patient's body, comprising:

(a) an elongate support member having a distal end portion and a proximal portion; and (b) a thin-walled probe-receiving tube of flexible material integral with and extending closely alongside said distal end portion of said support member, said tube having a closed distal end defining an interior space within said tube.

2. The device of claim 1 including a fluid conduit extending along said support member toward said distal end thereof and communicating, at a location proximate said distal end, with said interior space within said probe-receiving tube.

3. The device of claim 2 wherein said elongate support member is a drain tube having a wall thicker than a wall of said distal end of said probe-receiving tube and wherein said fluid conduit includes a lumen defined in said wall of said drain tube.

4. The device of claim 3 wherein said conduit includes a branch tube communicating with said lumen in said proximal of said support member, said branch tube having proximal end and a selectively openable closure associated with said closed end.

5. The device of claim 1 wherein said elongate support member is a drain tube including an opening for draining material from said location within said patient's body and wherein said probe-receiving tube includes a proximal portion at least part of which is unattached to said proximal portion of said elongate support member, said proximal portion of said probe-receiving tube having a wall which is thicker and substantially more difficult to collapse than said thin-walled distal portion.

6. The device of claim 1 wherein at least said distal portion of said probe-receiving tube is of material substantially transparent to ultrasound waves.

7. The device of claim 1 wherein said probe-receiving tube has an open proximal end.

8. The device of claim 1 wherein said distal end of said probe-receiving tube extends beyond said distal end portion of said elongate support member at least about 0.25 inch.

9. The device of claim 1 including structure defining a fastener passageway extending transversely of said device and located between said elongate support member and said probe-receiving tube in a location suitable for receiving a suture to attach said support member and said probe-receiving tube to said patient.

10. The device of claim 1 wherein said elongate support element is a drain tube for draining material from said patient's body and is of stiff, but resiliently flexible material, and wherein a distal portion of said probe-receiving tube is easily collapsible.

11. The device of claim 1 wherein said probe-receiving tube includes a friction-inhibiting coating of material on its interior surface.

12. The device of claim 1 wherein said elongate support member is a chest drain tube for draining material from said patient's chest.

13. The device of claim 12 wherein said chest drain tube is of non-circular cross-section shape and of thick-walled construction.

14. A method for enabling a sensor probe to be placed quickly in a desired location within a living patient, comprising:

(a) providing a probe-receiving tube having a flexible-walled, closed distal end portion integral with and located alongside and in close proximity with a relatively stiff elongate support member;

(b) thereafter inserting a distal portion of said support member together with said distal end portion of said tube into an interior cavity or a passageway into a body cavity of a living patient, leaving a proximal portion of said probe-receiving tube extending outside the patient;

(c) thereafter, temporarily inserting a sensor probe within said probe-receiving tube and into proximity with said distal end portion thereof, thereby placing said sensor probe in a desired location within said patient;

(d) utilizing said sensor probe to make a desired observation within said patient; and (e) thereafter removing said sensor probe from said probe-receiving tube, while leaving said support member and said probe-receiving tube in place within said interior cavity or passageway.

15. The method of claim 14 wherein said support member is a chest drain tube for draining material from said patient's chest cavity.

16. A method for enabling a sensor probe to be placed quickly in a desired location within a living patient, comprising:

(a) supporting a probe-receiving tube having a flexible-walled, closed distal end portion alongside and in close proximity with a relatively stiff elongate support member, said support member being a chest drain tube;

(b) inserting a distal portion of said support member and said distal end portion of said tube into an interior cavity or a passageway into a body cavity of a living patient and placing said distal end portion of said probe-receiving tube in proximity with the epicardium of said patient, leaving a proximal portion of said probe-receiving tube extending outside the patient;

(c thereafter, temporarily inserting a sensor probe within said probe-receiving tube and into proximity with said distal end portion thereof, thereby placing said sensor probe in a desired location within said patient;

d) utilizing said sensor probe to make a desired observation within said patient; and (e) thereafter removing said sensor probe from said probe-receiving tube, while leaving said support member in place within said interior cavity or passageway.

17. The method of claim 16 wherein said sensor is an ultrasound imaging transducer, including the steps of installing said chest drain tube and said probe-receiving tube during a surgical procedure normally requiring installation of a chest drain tube, and inserting said ultrasound imaging transducer into proximity with a patient's heart temporarily while said chest drain tube remains in place.

18. The method of claim 14 wherein said sensor probe is an ultrasound transducer, including the further step of providing a quantity of an acoustic coupling fluid within said probe-receiving tube together with said ultrasound transducer.

19. The method of claim 14 including the further steps of keeping said probe-receiving tube empty and collapsed when said sensor probe is not in place within said probe-receiving tube and inserting a sensor probe into said probe-receiving tube and into proximity with said distal end portion thereof at a substantially later time.

20. A device for use in a medical procedure for placing a sensor probe temporarily in a desired location within a patient's body, comprising a thin-walled probe-receiving tube of flexible biologically compatible material, said tube having an internal size large enough to accept an ultrasound scanning probe, and having a closed distal end, a distal end portion of said tube being flexibly collapsible, and a proximal portion of said tube having a greater wall thickness so as to resist collapse and facilitate introduction of a sensor probe into said probe-receiving tube.

* * * * *